United States Patent [19]
Long

[11] Patent Number: 5,407,275
[45] Date of Patent: Apr. 18, 1995

[54] NON-DESTRUCTIVE TEST FOR INNER LEAD BOND OF A TAB DEVICE

[75] Inventor: Jon M. Long, Livermore, Calif.

[73] Assignee: VLSI Technology, Inc., San Jose, Calif.

[21] Appl. No.: 860,932

[22] Filed: Mar. 31, 1992

[51] Int. Cl.⁶ .................. G01N 25/72; G01R 31/04
[52] U.S. Cl. .......................... 374/5; 374/45; 228/104; 228/105
[58] Field of Search ............... 228/103, 104, 105; 374/4, 5, 124, 137; 324/45

[56] References Cited

U.S. PATENT DOCUMENTS

| | | | |
|---|---|---|---|
| 3,803,413 | 4/1974 | Vanzetti et al. | 250/342 X |
| 4,682,605 | 7/1987 | Hoffman | 374/137 X |
| 4,813,588 | 3/1989 | Srivastava et al. | 228/103 |
| 5,052,816 | 10/1991 | Nakamura et al. | 374/5 |
| 5,080,279 | 1/1992 | Davison | 228/103 |
| 5,201,841 | 4/1993 | Lebeau et al. | 374/5 |

FOREIGN PATENT DOCUMENTS

| | | | |
|---|---|---|---|
| 0243574 | 12/1985 | Japan | 374/5 |
| 0126534 | 5/1989 | Japan | 374/4 |
| 0262455 | 10/1989 | Japan | 374/45 |

Primary Examiner—William A. Cuchlinski, Jr.
Assistant Examiner—Willie Morris Worth
Attorney, Agent, or Firm—Karen S. Perkins

[57] ABSTRACT

A method for testing a lead connection to an integrated circuit chip is disclosed. The method comprises the steps of: (a) applying heat to an exposed surface of the integrated circuit chip; and (b) determining the heat transferred from the integrated circuit chip to a lead. Rapid transfer of heat to the lead indicates a valid connection between the integrated circuit chip and the electrical lead. Slow, non-uniform, or inadequate transfer of heat to the lead indicates an insufficiency or failure in the electrical connection between the integrated circuit and the lead. Determination of the heat transferred from the integrated circuit chip to the lead can be by any appropriate method. For example, the temperature of the lead can be determined using temperature probe, a liquid crystal display, or an electronically or visually scanned infrared display.

10 Claims, 4 Drawing Sheets

NON-DESTRUCTIVE TEST FOR INNER LEAD BOND OF A TAB DEVICE

TECHNICAL FIELD

This invention relates to the testing of electrical connections, especially electrical connections between a semiconductor die and its electrical leads.

BACKGROUND OF THE INVENTION

Semiconductor devices communicate with their environment by accepting electrical impulses supplied by an external circuit (such as on a circuit board) and conducting these impulses to electrical circuits contained on a semiconductor chip. The semiconductor chip reacts to the input impulses in a predetermined manner to generate output electrical impulses. These output electrical impulses are then sent from the chip to an external circuit (e.g., on the circuit board). The input and output of electrical impulses to the semiconductor device occur over multiple paths of electrically conducting material, commonly referred to as leads.

The connections between the integrated circuit die and the leads can be made by wire bonding, in which a thin connecting wire is bonded at one end to the die input or output, and at the opposite end to the electrical lead. When wire bonding is used to connect an integrated circuit and its associated leads, a protective rigid housing is often added to enclose and protect the fragile connecting wires.

Alternatively, the connections between the integrated circuit die and the leads can be made by tape automated bonding (TAB) connections, in which a bead of conductive material connects the die input or output to the electrical lead. As shown in FIG. 1a, such semiconductor device packages 10 generally have a flexible tape substrate 12 that includes an insulative layer, and lead layer including a plurality of electrical leads. An integrated circuit chip 18 is attached approximately medially within the package. The view of FIG. 1b (taken through line 1b—1b of FIG. 1a) shows the semiconductor device package 10 in cross-section. The tape substrate 12 includes a patterned insulative layer 14, and a patterned conductive layer, or lead layer 16, including a plurality of electrical leads 17. An integrated circuit chip 18 which has at least one exposed surface 20 is connected to the lead layer 16 with a connective bead 22. An electrically nonconductive protective material 23, such as a standard semiconductor packaging encapsulant, can be present to maintain the integrated circuit chip 18, the lead layer 16, and the connective bead 22 in relative position. A rigid supporting member (not shown) can be present surrounding the periphery of the tape substrate 12.

A variety of manufacturing or handling-induced failures can cause failure of the electrical connection between the integrated circuit chip 18 and its associated electrical leads 17. An integrated circuit chip 18 can have a malformed or non-functional input/output site. A connecting TAB bead 22 can be absent or malformed, or can have internal impurities that reduce the conductivity of the connection between the integrated circuit chip 18 and the electrical lead 17. Ink, dust, or other surface contaminants present on the surface of the integrated circuit chip 18, the connective bead 22, or the electrical lead 17 can restrict or eliminate conductivity between the integrated circuit chip 18 and the electrical lead 17. The electrical leads 17 can be malformed, or can break due to mishandling. An abrupt shock can cause breakage or separation of the connective link between the integrated circuit chip 18, the connective bead 22, or the electrical lead 17, even if the lead connections had been previously tested and found to be adequate.

Prior art testing methods for packaged integrated circuit devices are time consuming, and most methods result in the destruction of the device tested. For example, lead connections can be tested after packaging by removal of any encapsulant, and conducting a pull test on the bonds. A non-destructive alternate method uses a Slam microscope to determine lead connection integrity. However, such microscopes require trained personnel, are difficult to interpret, and are prohibitively expensive for generalized screening.

SUMMARY OF THE INVENTION

Electrically conductive leads and lead connections are good thermal conductors. When an integrated circuit chip is connected properly to a lead by TAB methods, both thermomechanical and electrical connections are present. An inadequate or interrupted electrical conduction is characterized by an inadequate or interrupted thermal conduction. The testing method of this invention uses a test of the thermomechanical properties, specifically, of the heat-conductive characteristics, of a lead within the integrated circuit package to determine the presence of an effective electrical connection to that lead.

A method for testing a lead connection to an integrated circuit chip is disclosed. The method comprises the steps of: (a) applying heat to an exposed surface of the integrated circuit chip; and (b) determining the heat transferred from the integrated circuit chip to a lead. Rapid transfer of heat to the lead indicates a valid connection between the integrated circuit chip and the electrical lead. Slow, non-uniform, or inadequate transfer of heat to the lead indicates an insufficiency in the electrical connection between the integrated circuit and the lead.

Determination of the heat transferred from the integrated circuit chip to the lead can be by any appropriate method. For example, the temperature of the lead can be determined using a temperature probe, a liquid crystal display, or an infrared sensor.

DISCLOSURE OF THE INVENTION INCLUDING BEST MODE

Figure 1B:
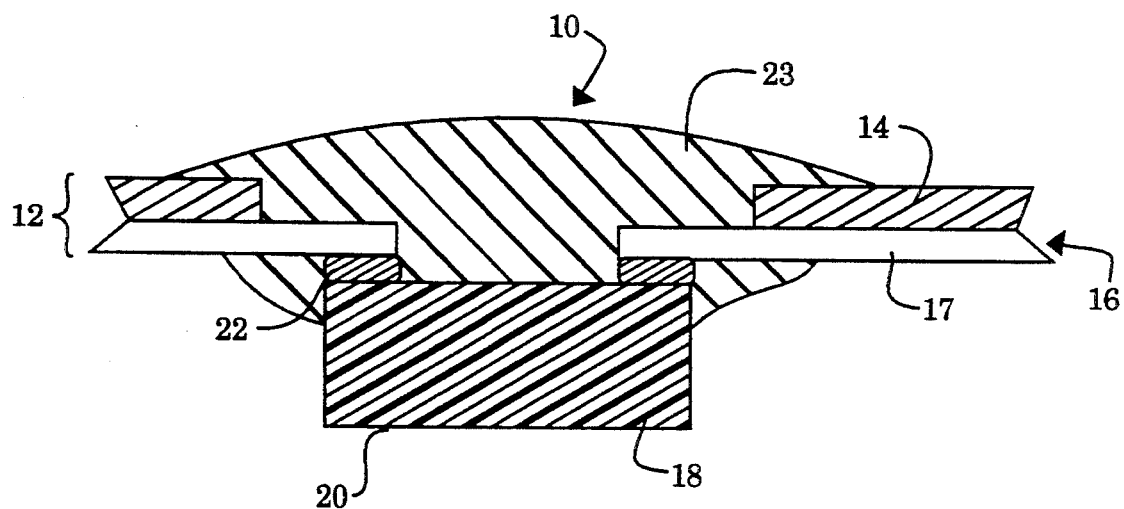
FIG. 1 shows an integrated circuit package in top view (FIG. 1a) and in cross-sectional view (FIG. 1b).
Figure 1A:
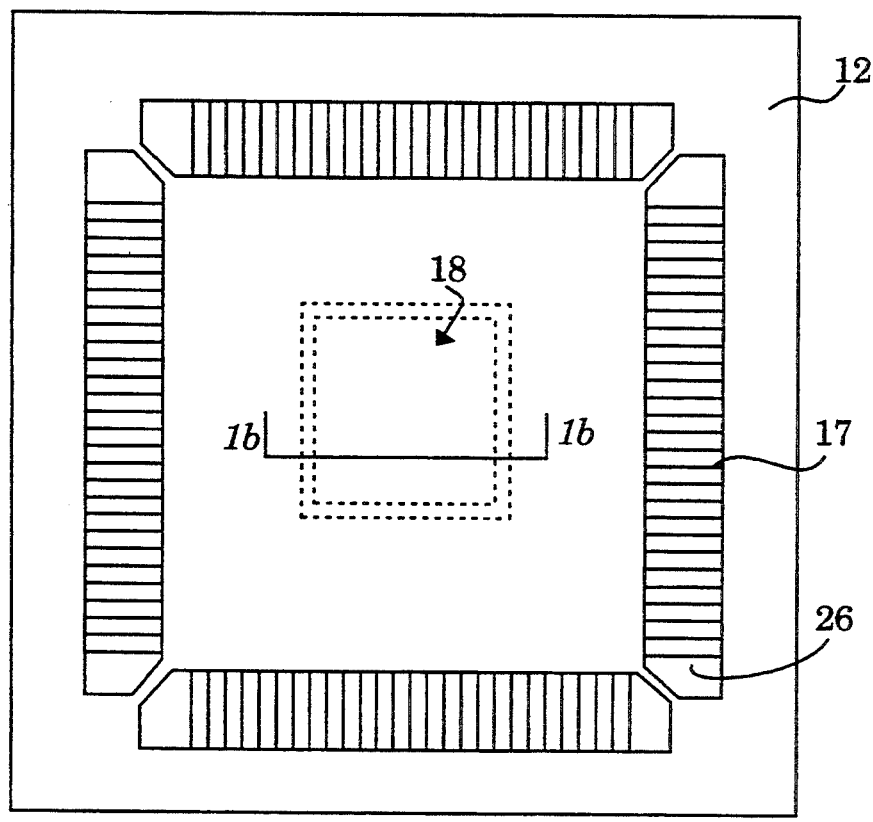
Figure 2A:
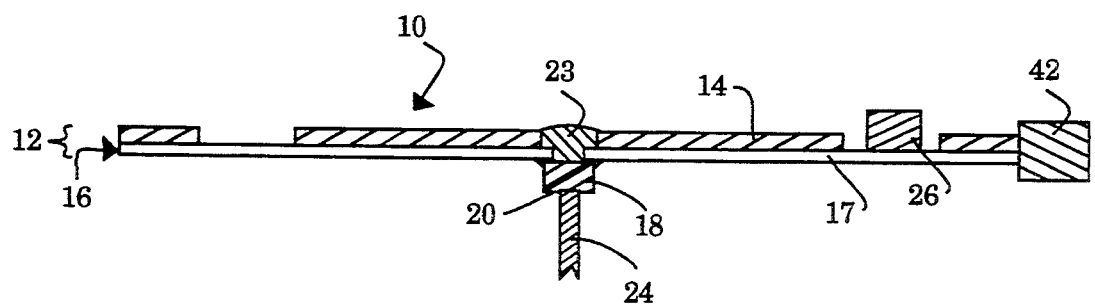
FIG. 2 an integrated circuit package, a heater device, and a temperature testing device in cross-sectional view (FIG. 2a) and in top view (FIG. 2b).
Figure 2B:
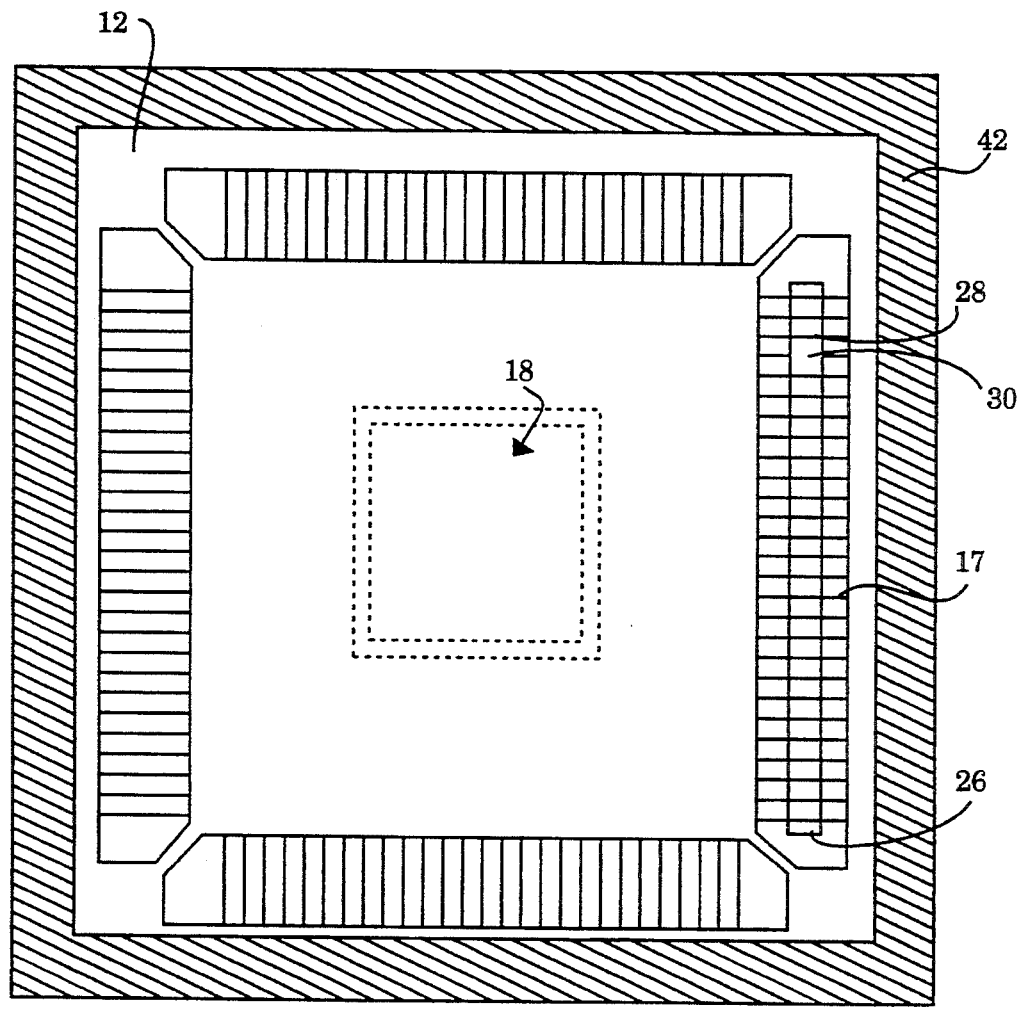

As shown in FIGS. 2a and 2b, a semiconductor device package 10 such as those amenable to the testing methods of this invention includes a tape substrate 12 having a patterned insulative layer 14, a patterned conductive layer, or lead layer 16, including a plurality of electrical leads 17, and an integrated circuit chip 18 which has at least one exposed surface 20. The integrated circuit chip 18 is connected to individual leads 17 with connective beads (not shown). An electrically nonconductive protective material 23 can be present. A rigid holder 42 can be present to provide handling strength for the semiconductor device package 10.

The tape substrate 12 provides a suitable electrical connection between the integrated circuit chip 18 and the environment of use. Two- and multiple-layered tape substrates 12 which are appropriate for use herein are well known in the art and are available from, for example, Shindo Co. (Japan), 3M (Minnesota), and Mitsui Metal Mining Co. (Japan). Tape substrates 12 which are appropriate are sold as "two-layer" and "three-layer" tapes. Generally, "two-layer" tape has a patterned metal layer bonded directly to a patterned insulative layer. The examples used herein generally refer to two-layer tapes. "Three-layer" tape has a patterned metal layer bonded to a patterned insulative layer with an intermediate adhesive layer.

The patterned insulative layer 14 is generally made of a flexible insulative material. Thermoset plastics such as epoxies can be used. Durable polyimide plastics are preferable for use. Polyimide films are available commercially as Kapton ™ (Dupont Chemicals) and Upilex ™ (UPI, Japan, available through Shindo Denshi, Japan). The patterned insulative layer 14 does not form a continuous surface, but rather is patterned with voids and planes of different shapes and sizes to provide a combination of conductive regions (encompassing a void through which the conductive layer is accessible) and insulative regions (encompassing a surface which insulates and isolates the conductive layer). The patterned insulative layer 14 generally has a thickness of from less than about 2 mill to more than about 5 mil, more preferably from about 3 mil to about 5 mil.

The lead layer 16 is made of a conductive material, generally a metal. The metal used will generally depend upon the desired conductive attributes and cost. Copper, gold, nickel, lead, tin, and alloys or combinations thereof leads are appropriate. The lead layer 16 is patterned to provide a plurality of electrical leads 17 which extend between the periphery of the integrated circuit chip 18 and the periphery of the completed package 10. The innermost edges of the electrical leads 17 are generally connected to input or output connections on the integrated circuit chip 18. The outermost edges of the electrical leads 17 are the package leads, and these provide the connection between the completed integrated circuit chip package and the environment in which the integrated circuit chip finds its ultimate use.

The integrated circuit chip 18 can have any desired use or configuration. The specific pattern of the insulative layer and the lead layer can vary with the integrated circuit die, its intended use, and the method of affixing the integrated circuit die to the tape substrate. The integrated circuit chip 18 will generally include at least one surface 20 which is exposed or otherwise available for heating by the heat source 24. Conveniently, the exposed surface can be the surface opposite that surface at which the TAB connections are made, however this is not critical. The exposed surface 20 need not be completely exposed to the environment. However, the exposed surface 20 should not include any thermal conductors which would act to transmit heat from the heat source 24 quickly to the leads 17 without first passing through the TAB bonds.

The leads of the lead layer are connected both mechanically and electrically to the integrated circuit chip 18 using TAB processes. In such methods, a conductive bead 22 is positioned between an integrated circuit output or input location on the integrated circuit chip 18 and an electrical lead 17. A multiplicity of such conductive beads 22 connect each input or output to a corresponding lead. Generally, a multiplicity of connecting beads 22 are connected to their individual inputs or outputs, and their electrical leads 17, by positioning the connecting beads 22 and the electrical leads 17 adjacent to the input or output, and heating the connecting beads 22 under pressure. The connecting beads 22 are generally made of a conductive material, generally a metal. The metal used will depend upon the desired connecting bead 22 attributes. Copper, gold, nickel, lead, and tin connecting beads 22 are generally appropriate. Gold connecting beads 22 are particularly appropriate.

Generally, an electrically nonconductive protective material 23 is present surrounding the TAB bond, to maintain the integrated circuit chip 18, the lead layer 16, and the connective bead 22 in relative position. The electrically nonconductive protective material 23 is also substantially thermally nonconductive. Suitable materials for use as the electrically nonconductive protective material 23 include encapsulants such as epoxies (available from Dexter Hysol, City of Industry; or Hokuraiku, Japan) and silicones (available from Dow Corning). Preferably, additional packaging structures which readily act as heat conductors, such as rigid plastic or metallic enclosing structures, are minimized or absent.

FIG. 2 illustrates the method of this invention. The integrated circuit chip 18 is heated, generally by contacting a heat source 24 to an exposed surface 20 of the integrated circuit chip 18. Heat is transferred from the heat source 24 to the integrated circuit chip 18. The heat energy passes through the TAB connective bead 22, and across the electrical leads 17. The flow of heat from the heat source 24, across the electrical connections, and through the electrical leads 17 is determined by measuring the temperature of the leads 17.

The heat source 24 is generally a heating probe or a similar implement in which the temperature can be regulated and applied selectively to a specific exposed area of the integrated circuit chip 18. The temperature to which the integrated circuit chip is heated is not critical. However, the integrated circuit chip will generally be heated to a temperature which is more than about 100° C. greater than ambient temperature. Heating the integrated circuit chip to temperatures of 175° C. and above will result in the destruction of the integrated circuit chip and/or of the packaging. Generally, the integrated circuit chip is heated to a temperature of from less than about 40° C. to more than about 125° C., more generally from about 80° C. to about 100° C. The heat energy which is applied to an exposed surface of the integrated circuit chip is transmitted through the electrical connections of the package, and to the leads, causing the temperature of the leads to increase.

Heat which is applied to the exposed surface 20 of the integrated circuit chip 18, is transmitted substantially and quickly through the intact lead connections. A secondary warming of improperly connected leads will gradually occur as the packaging materials are warmed, which can lead to false "pass" results. This secondary warming of improperly connected leads is significantly slower than the warming of leads with intact lead connections, however.

The specific time range for testing the temperature of the leads will vary with the specific integrated circuit package being tested, the ambient temperature, and the temperature of the warming device used to heat the integrated circuit chip. For example, at ambient temperatures of about 25° C., using a heater at 100° C. to heat the exposed surface of an Intel 386 semiconductor chip, the leads can be accurately tested after about 0.5 seconds from contact of the heat source. Lead temperatures measurements should be completed within about 10 seconds of heat source contact, as temperature testing of the leads becomes less accurate with increased passage of time.

If an integrated circuit package is warmed and no temperature reading is taken, the package merely has to be cooled to ambient temperatures before the testing process can be repeated.

The temperature of the electrical leads 17 can be determined using any of a variety of determining methods. For example, a temperature probe can be contacted to a lead to determine its temperature. In a preferred embodiment, a thermosensitive liquid crystal layer is placed across one or more leads, and the temperature at the leads is determined visually based upon changes in the liquid crystal. Alternatively, the temperature can be measured using an infrared scanning device, or the like. Determination of the temperature can be by direct operator observation, or by computer or electronic temperature information synthesis.

In one preferred embodiment, as shown in FIG. 2, a substrate strip coated with a liquid crystal material 26 is placed in direct contact with the electrical leads 17. Liquid crystal materials are commonly available in colorisotic or clearing forms. Colorisotic liquid crystal material demonstrates a color change (e.g., black to green) at a specific temperature. Clearing liquid crystal material demonstrates a visual density change (e.g., dark to clear) at a specific temperature.

Strips of liquid crystal material having a wide range of activation temperatures are available commercially from a variety of vendors. As shown in FIG. 2a and FIG. 2b, a strip of commercially available liquid crystal material 26 can be placed in direct contact with the leads of an integrated circuit package to provide a readout of the temperature of the leads. Alternately, individual leads can be tested with individual strips of liquid crystal material, or individual leads can be coated with liquid crystal material in a fluid form.

The specific liquid crystal material used will be a function of the temperature expected for intact lead connections, or a function of the temperature expected for incomplete lead connections. The temperature at the leads will be a function of the temperature of the temperature applied to the integrated circuit chip 18 at the heat source (not shown), the ambient temperature, the presence or absence of a heat sink, and the passage of time.

Heat is applied to an exposed surface of the integrated circuit chip 18, and the change of temperature in the leads 17 is reflected by the change of color of the liquid crystal material 26. Leads which include intact electrical and thermomechanical connections to the integrated circuit chip 18, and thus to the heat source (not shown) will become warmed quickly. Leads in which electrical and thermomechanical connections to the integrated circuit chip 18 have been severed or malformed will become warmed slowly, if at all. The varying temperatures of the intact or failed lead connections are reflected in the colors shown by the liquid crystal material 26. This change in color can be determined visually. As shown in FIG. 2b, the liquid crystal material 26 can be selected such that intact electrical connections 28 show a distinct color change, and failed electrical connections 30 show no color change. In an alternate embodiment, not shown, the liquid crystal material can be selected such that intact electrical connections show no color change, or no clearing, and failed electrical connections show a distinct color or clearing change.

In an alternate preferred embodiment (not shown), the leads of a semiconductor device to be tested are coated directly with a fluid liquid crystal material, according to manufacturers directions. As with liquid crystal strips, the varying temperatures of the intact or failed lead connections are reflected in the colors shown by the liquid crystal material. This change in color can be determined visually. After visual determination of the lead connections, chip packages which pass (i.e., chip packages in which all lead connections are valid) can be rinsed with an acetone rinse to remove the liquid crystal material and used as desired.

Figure 3A:
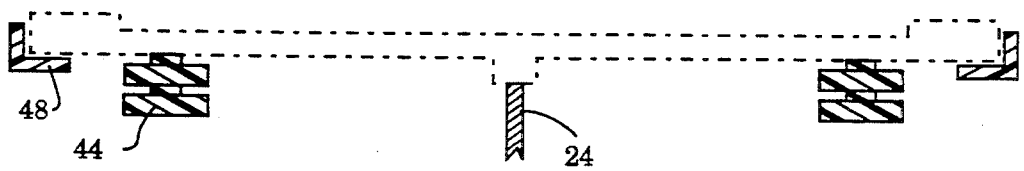
FIG. 3 shows cross-sectional views of a station of an automated infrared scanning device for testing integrated circuit packages. An empty station is shown in FIG. 3a. A test piece is loaded and heated in FIG. 3b. The automated detection step is shown in FIG. 3c.

FIG. 3 shows a cross-sectional view of an automated infrared scanning device for testing integrated circuit packages. An empty station is shown in FIG. 3a. A holding mechanism 48 for secure placement and positioning of the semiconductor device package 10 is preferably present. One or more heat source 24 is located to make contact when a semiconductor device package (not shown) is placed in position.

Preferably, one or more heat sink 44 is also positioned to make direct mechanical contact when a semiconductor device package (not shown) is placed in position. The heat sinks 44 function to cool the leads, and provide better discrimination of passing and failing lead temperatures. The detection means will generally be located medially between the heat source and the heat sinks.

Figure 3B:
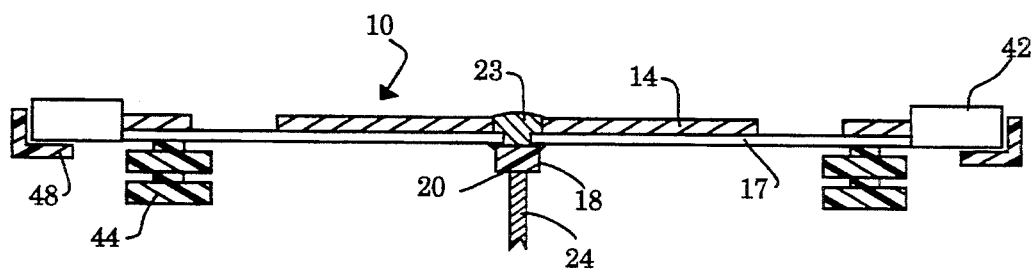

As shown in FIG. 3b, a semiconductor device package is placed into position at the station. The semiconductor device package can be positioned manually or automatically.

One or more heat source 24 and, preferably, one or more heat sink 44, is placed in direct mechanical contact with the semiconductor device package 10. The semiconductor device package 10 includes a tape substrate having a patterned insulative layer 14, a lead layer including a plurality of electrical leads 17, and an integrated circuit chip 18 which has at least one exposed surface 20. The integrated circuit chip 18 is connected to individual leads 17 of the lead layer with a multiplicity of connective beads (not shown). An electrically nonconductive protective material 23 can be present. A rigid holder 42 can be present to complete the semiconductor device package 10.

After or with the positioning of the semiconductor device package 10, heat is applied to the integrated circuit chip 18. Heat is transferred from the heat source 24 to the integrated circuit chip 18. The heat is then conducted through the TAB connective beads (not shown), and across the electrical leads 17.

Figure 3C:
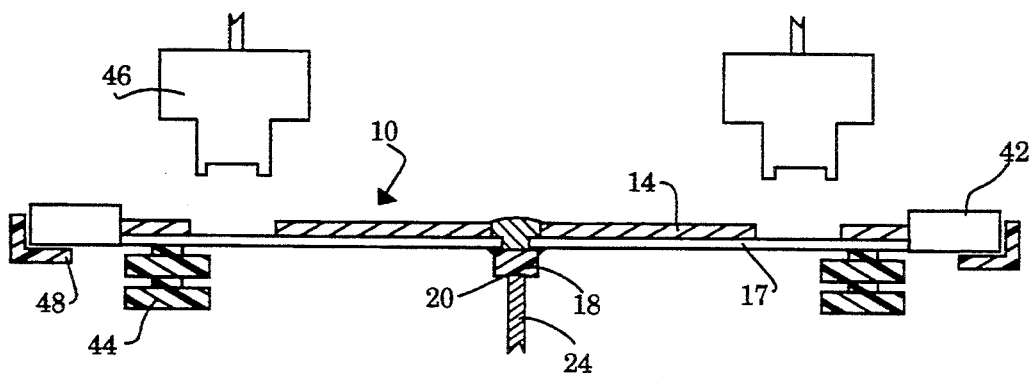

As shown in FIG. 3c, an infrared camera 46 is positioned above the electrical leads. The flow of heat from the heat source 24, across intact electrical connections, and through the electrical leads 17 is determined using an infrared temperature detection apparatus. In such an apparatus, an infrared camera 46 captures a thermographic image of the lead or leads of interest, and the thermographic image is transferred to a suitable imaging system (not shown). The thermogram images the temperature(s) visible to the infrared camera, separating temperature by color enhancement. A monitor can be used to allow an operator to visually determine whether a particular test piece passes or fails. Alternatively, the thermographic image can be digitized, and an automated analysis of the thermogram can be done, leading to an automated pass/fail determination.

In an additional step (not shown) the semiconductor device package is offloaded from the testing station, either manually or automatically.

Figure 4:
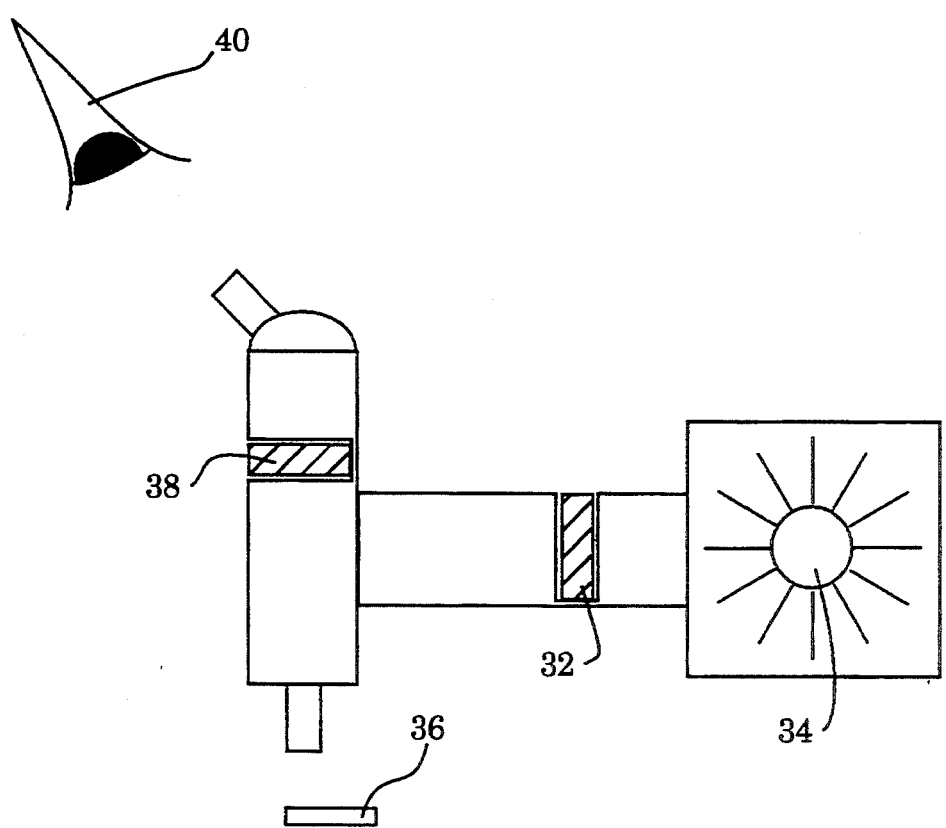
FIG. 4 shows a polarizing microscope device which can be used in a determination of lead temperature variation.

While some types of liquid crystal materials are easily determined using the unaided eye, or under standard magnification, it may be desirable to use a liquid crystal in conjunction with a polarized light microscope, such as that shown in FIG. 4. In such a system, a first polarizing light filter 32 is inserted between a light source 34 and the object observed 36. A second polarizing light filter 38 is placed between the object observed 36 and the observer 40. Heat is applied to an exposed surface of the integrated circuit chip 18, and the change of temperature in the leads 17 is reflected by the change in the liquid crystal material 26 as displayed under polarized light. Suitable liquid crystal materials and polarizing microscope equipment is available through Technology Associates, Portola Valley, Calif.

The determination of heat transfer through the leads can be automated. Vision systems (e.g., which determine the color of a colorisotic liquid crystal, which determine the color density of a clearing liquid crystal, or which determine temperature directly using an infrared detection system) can be used in temperature determining systems. The pass/fail determination is made using known vision system apparatus.

While the invention has been described in connection with several exemplary embodiments, it will be understood that many modifications will be apparent to those of ordinary skill in the art in light of the above disclosure. Such modifications may include using substitute materials, smaller or greater dimensions, more than one die in a package, a variety of different shapes for conductors, insulators and so forth, to achieve substantially the same results in substantially the same way. Reference to the following claims should be made to determine the scope of the claimed invention.

I claim:

1. A method for testing a lead connection in an integrated circuit chip, said method comprising:
   (a) applying heat to an exposed surface of an integrated circuit chip; and
   (b) determining the heat transferred from the integrated circuit chip to a lead by determine the heat transferred at a point on the lead which is distal from the connection under test.

2. A method of claim 1 wherein heat transfer is determined using a thermometer.

3. A method of claim 1 wherein heat transfer is determined using a liquid crystal thermal medium to determine the temperature of the lead.

4. A method of claim 1 wherein heat transfer is determined by determining lead temperature using an infrared temperature sensing to determine the temperature of the lead.

5. A method of claim 1 wherein heat transfer is determined using a temperature probe to determine the temperature of the lead.

6. A method of testing a packaged semiconductor device to determine the electrical connection between the integrated circuit chip and a lead, the electrical connection to the lead being tested by:
   (a) applying heat to an exposed surface of the packaged integrated circuit chip; and
   (b) determining temperature increase at an exposed point on the lead.

7. A method of claim 6 wherein heat transfer is determined using a thermometer.

8. A method of claim 6 wherein heat transfer is determined using a liquid crystal thermal medium to determine the temperature of the lead.

9. A method of claim 6 wherein heat transfer is determined by determining lead temperature using an infrared temperature sensing to determine the temperature of the lead.

10. A method of claim 6 wherein heat transfer is determined using a temperature probe to determine the temperature of the lead.

* * * * *